United States Patent [19]

Irgang et al.

[11] Patent Number: 5,714,644
[45] Date of Patent: Feb. 3, 1998

[54] PROCESS AND CATALYST FOR THE SELECTIVE HYDROGENATION OF BUTYNEDIOL TO BUTENEDIOL

[75] Inventors: Matthias Irgang, Heidelberg; Volkmar Menger, Neustadt; Ernest Miesen, Ludwigshafen; Peter Stops, Altrip; Fritz Graf, Speyer, all of Germany

[73] Assignee: BASF Aktiengesellschaft, Ludwigshafen, Germany

[21] Appl. No.: 765,215

[22] PCT Filed: Jul. 4, 1995

[86] PCT No.: PCT/EP95/02592

§ 371 Date: Mar. 20, 1997

§ 102(e) Date: Mar. 20, 1997

[87] PCT Pub. No.: WO96/01242

PCT Pub. Date: Jan. 18, 1996

[30] Foreign Application Priority Data

Jul. 6, 1994 [DE] Germany .......................... 44 23 738.3

[51] Int. Cl.$^6$ .................................................. C07C 31/18
[52] U.S. Cl. ..................................... 568/857; 502/329
[58] Field of Search .............................. 568/857; 502/329

[56] References Cited

U.S. PATENT DOCUMENTS

| | | | |
|---|---|---|---|
| 2,953,605 | 9/1960 | Hort et al. | 568/861 |
| 3,119,879 | 1/1964 | Hort et al. | 568/857 |
| 3,450,776 | 6/1969 | Di Cio et al. | 568/857 |
| 4,001,344 | 1/1977 | Hoffmann et al. | 568/857 |
| 4,021,374 | 5/1977 | Petro et al. | 502/328 |
| 4,273,944 | 6/1981 | Ohno et al. | 568/396 |
| 4,658,071 | 4/1987 | Seufert et al. | 568/903 |
| 5,015,788 | 5/1991 | Toussaint et al. | 568/861 |

FOREIGN PATENT DOCUMENTS

| | | |
|---|---|---|
| 1090829 | 12/1980 | Canada . |
| 011 439 | 5/1980 | European Pat. Off. . |
| 312 253 | 4/1989 | European Pat. Off. . |
| 832 141 | 4/1960 | United Kingdom . |
| 871 804 | 6/1961 | United Kingdom . |

OTHER PUBLICATIONS

Derwent Abstract No. 81-82217D (English abstract of JP 56 12 0627, Sep. 22, 1981).

*Primary Examiner*—Bernard Dentz
*Assistant Examiner*—Garth M. Dahlen
*Attorney, Agent, or Firm*—Keil & Weinkauf

[57] ABSTRACT

A process is disclosed for the selective hydrogenation of butynediol to 2-butene-1,4-diol using a palladium catalyst to which either copper and zinc, or silver and zinc, or copper, silver and zinc are added as doping agents. In the preferred embodiment, it has been possible, by optimizing the composition of the catalyst, to improve the activity and selectivity of the catalysts in question while also eliminating the need to handle toxic substances during the catalyst manufacturing process.

10 Claims, No Drawings

PROCESS AND CATALYST FOR THE SELECTIVE HYDROGENATION OF BUTYNEDIOL TO BUTENEDIOL

This application is a 371 of PCT/EP95/02592, Jul. 4, 1995.

2-Butene-1,4-diol (referred to below as "butenediol") has been produced for some time on an industrial scale from 2-butyne-1,4-diol (referred to below as "butynediol"), which is produced on an industrial scale by the Reppe synthesis. Butenediol is required for some important crop-protection agents, pharmaceuticals and intermediates. It is of great importance that a very pure hydrogenation product is obtained, since product losses must be avoided and distillative removal of unhydrogenated butynediol and of butanediol formed by overhydrogenation is only possible in a complex procedure.

The catalytic hydrogenation of butynediol to butenediol is generally carried out batchwise using a suspension catalyst. In this process, hydrogen at 30°–150° C. and 1–20 bar is injected into a stirred reactor containing the butynediol solution and catalyst. The reaction is terminated when the stoichiometric amount of hydrogen has been taken up. Numerous proposals have been made regarding the catalysts, in particular palladium catalysts, and some have also been implemented in industry.

In order to achieve adequate selectivity, $Pd/BaSO_4$ catalysts with addition of quinoline (DE 1 115 238), $Pd/Al_2O_3$ catalysts with addition of carbon monoxide (DE 2 619 660) and Pd/Cu and $Pd/Al_2O_3$ catalysts with addition of copper acetate (GB 832 141) have been proposed.

However, soluble additives are inconvenient to handle and cause problems during work-up. Metering in of CO, as described in DE 2619 660, requires additional technical complexity and should therefore be avoided.

According to information in patents, good results have also been achieved with the following catalysts:
5% of $Pd/BaSO_4$ DE 2 605 241
5% of $Pd/Al_2O_3$ doped with lead acetate DE 2 818 260
5% of $Pd/BaSO_4$ with addition of copper nitrate DD 246 986
In spite of the use of high-percentage catalysts (5% of Pd), long hydrogenation times were necessary for these hydrogenations.

DE 2 431 929 describes catalysts containing only 0.5% of Pd on $Al_2O_3$ with zinc, cadmium, bismuth and tellurium doping. The catalysts have good selectivity, but have the disadvantage of containing carcinogenic or toxic constituents.

A particular difficulty arises if crude butynediol is to be employed in the selective hydrogenation without prior purification. This material having a pH of about 5 contains methanol, formaldehyde, formic acid and propargyl alcohol. It also contains catalyst constituents, such as Cu and Bi, from the butynediol synthesis. The catalyst thus also needs to have substantial tolerance to these constituents of the starting material, although it is known that both added copper (cf. DD 246 986) and added bismuth (cf. DE 2 431 929) affect the hydrogenation.

In spite of the extensive prior art, there is a desire for a further improvement in the process for the selective hydrogenation of butanediol and in the catalyst which can be used for this purpose. The invention has the object of solving the following problems or part-problems—individually or in combination:

1. No toxic or carcinogenic substances, such as, for example, compounds of tellurium or cadmium, should be employed in the preparation of the catalyst.

2. The highest possible selectivity should be achieved in order to minimize product losses, in particular due to overhydrogenation and acetal formation.

3. A high catalyst activity should be achieved in order to reduce the amount of catalyst employed, based on the amount of butynediol to be reacted.

4. Simple handling of the catalyst, in particular good filterability, should be achieved.

5. It should also be possible to carry out the selective hydrogenation using crude butynediol (in particular having a pH of 5).

6. It should also be possible to carry out the selective hydrogenation in the presence of one or more of the following contaminants: methanol, formaldehyde, formic acid, propargyl alcohol or Cu and/or Bi, which can originate, for example, from the butynediol synthesis.

7. Tolerance of the catalyst to constituents of the starting material.

These problems or part-problems of the invention are solved by means of processes and catalysts as defined in the claims. Preferred embodiments of the invention are shown in the subclaims and in the following description and the examples. In addition to palladium and zinc, the catalyst according to the invention also contains copper or silver, but expediently contains no cadmium. With respect to its active constituents, the catalyst preferably consists of these elements (Pd+Zn+[Cu and/or Ag]) and contains no other active constituents. The preferred catalyst is a supported palladium catalyst containing said active constituents. All amounts regarding metal oxides herein should be regarded as amounts based on the metal as the relevant oxide. The actual structure may differ from that stated.

In accordance with the invention, a process has been found for the preparation of 2-butene-1,4-diol by selective hydrogenation of butynediol in the presence of a palladium catalyst, wherein, in addition to palladium, the catalyst also contains the elements zinc and copper or zinc and silver or zinc and copper and silver.

The supported catalyst which can be used according to the invention for the hydrogenation of butyne-1,4-diol to butene-1,4-diol generally contain from 0.1 to 7% by weight of palladium, preferably from 0.1 to 4% by weight of palladium, in each case calculated as Pd and based on the total weight of the catalyst, in their catalytically active material. As further catalytically active elements, the catalyst to be used according to the invention also contains, in addition to palladium, the elements zinc and copper or zinc and silver or zinc and copper and silver.

In addition to palladium in the abovementioned amounts, catalysts which can be used according to the invention and which comprise the catalytically active components palladium, zinc and copper in their catalytically active material contain the two other elements in amounts which correspond to a palladium:zinc atomic ratio of, generally, from 10:1 to 1:4 and a zinc:copper atomic ratio of, generally, 5:1 to 1:2.

In addition to palladium in the abovementioned amounts, catalysts which can be used according to the invention and which comprise the catalytically active components palladium, zinc and silver in their catalytically active material contain the elements zinc and silver in amounts which correspond to a palladium:zinc atomic ratio of, generally, from 10:1 to 1:4 and a zinc:silver atomic ratio of, generally, 5:1 to 1:2.

In addition to palladium in the abovementioned amounts, catalysts which can be used according to the invention and which comprise the catalytically active components palladium, zinc, copper and silver in their catalytically active material contain the elements zinc, copper and silver in amounts which correspond to a palladium:zinc atomic ratio of, generally, from 10:1 to 1:4, a zinc:copper atomic ratio of, generally, from 5:1 to 1:2 and a zinc:silver atomic ratio of, generally, 5:1 to 1:2.

The catalysts which can be used according to the invention are supported catalysts. Preferred supports are materials of low acidity or basic supports. Examples of advantageous support materials are aluminum oxides, calcium carbonate, magnesium oxide, spinel ($MgAl_2O_4$), barium sulfate, titanium dioxides and zirconium dioxide. The catalysts which can be used according to the invention can also be prepared using mixtures of these support materials. A particularly preferred support material is aluminum oxide, in particular δ-aluminum oxide, which can be prepared as described in Ullmanns Encyklopädie der technischen Chemie, 4th Edn., Volume 7, pp. 298–299, Verlag Chemie, Weinheim, 1974. A particularly suitable δ-aluminum oxide support material has been found to be δ-aluminum oxide having a BET surface area of 100 to 130 $m^2/g$ (measured by the method of C. N. Satterfield, Heterogeneous Catalysis in Practice, pp. 102–105, New York 1980) and having a particle size of from 100 to 200 μm, which has particularly good settling and filtration properties and results, when used as support material, in only low acetal and polymer formation. In general, however, the support materials used have a BET surface area of 5 to 200 $m^2/g$, a porosity of 0.1 to 1 ml/g, determined by water absorption, and a mean particle size of from 20 to 150 μm with a maximum particle size of up to 300 μm.

Particularly advantageous catalysts have proven to be those prepared by impregnating the support material with a solution of the catalytically active catalyst components. The impregnation of the support can be carried out simultaneously by impregnation with a mixed solution of water-soluble salts of the catalytically active components, preferably with a solution of their nitrates or acetates, or by sequential impregnation with solutions of in each case one of these salts, the impregnated support expediently being dried after the individual impregnation steps. The impregnation can be accomplished by treating the support material with a supernatant solution of these salts, particularly advantageously by adding a mixed solution to the support in a rotating drum, it being advantageous to use an amount of solution which corresponds to the pore volume of the support. After drying and, if desired, calcination, in general at from 300° to 600° C., preferably at from 400° to 550° C., the catalyst can be employed in the novel process. The catalysts can be activated before use in the novel process, for example by treatment with hydrogen or other reducing agents, such as hydrazine, but this is generally unnecessary since these catalysts can advantageously be reduced and activated in situ in the reaction mixture.

It has now been found, surprisingly, that copper- and zinc-doped palladium on aluminum oxide catalysts have significantly higher selectivity in the novel process than a catalyst containing only palladium and copper. This allows a significant increase in the butenediol yield. In particular, these Pd/Zn/Cu catalysts allow the total amount of the byproducts butynediol, butanediol and acetals in the novel process to be reduced to a level below that of the Pd/Zn/$Al_2O_3$ and Pd/Zn/Cd/$Al_2O_3$ catalysts of the prior art.

Other very selective catalysts in the novel process have proven to be silver- and zinc-doped palladium on aluminum oxide catalysts. The use of basic supports, such as calcium carbonate or magnesium oxide, allows a further increase in the yield to be achieved in the novel process, the amount of acetal byproducts formed being further reduced.

These catalysts achieve the objects of the novel process. In particular, the use of these catalysts allows particularly high space-time yields to be achieved and the formation of byproducts to be minimized. In addition, they are easy to handle with respect to environmental protection and workplace safety.

The selective hydrogenation of butynediol to butenediol can be carried out by means of the catalysts to be used in accordance with the invention by hydrogenation techniques which are conventional per se. The catalysts are preferably employed in suspended form in the reaction mixture. The hydrogenation can be carried out at atmospheric pressure or under superatmospheric pressure. In general, a pressure of from 1 to 20 bar, preferably from 1 to 10 bar, and a temperature of, generally, from 20° to 150° C., preferably from 50° to 120° C., are used.

The starting material used can be pure butynediol or solutions thereof in a suitable solvent, for example water, but the novel process is preferably carried out using crude butynediol solution as produced, for example, in the butynediol preparation by the Reppe method. This crude butynediol generally contains about 50% by weight of water, from 1.5 to 2.5% by weight of impurities from the Reppe synthesis. Although these impurities tend to form byproducts and tar-like residues during hydrogenation, this formation of byproducts and residues can be minimized with the aid of the catalysts to be used in accordance with the invention.

The hydrogen can be fed to the hydrogenation reactor, preferably a stirred reactor with gas dispersion stirrer, in a stoichiometric or excess amount, preferably a stoichiometric amount, with respect to the butynediol.

For work-up, the reaction mixture is generally distilled, expediently after prior removal of the catalyst, for example by filtration or centrifugation.

It is expedient here first to remove water and an initial cut containing predominantly allyl alcohol. This is expediently followed by removal of the butenediol together with the byproducts butanediol, butynediol and acetals from the high-boiling residue by distillation, after which the butenediol can be isolated in a final purification distillation step.

The novel process can be carried out either batchwise, for example in stirred autoclaves, or continuously, for example in stirred reactor cascades. The process is preferably carried out batchwise.

EXAMPLES

The % by weight data in the examples are based on the entire catalyst as 100% by weight.

Catalyst A (Comparative Example)

5 kg of δ-$Al_2O_3$ having a particle size of 100–200 μm were introduced into a rotating drum and sprayed with a mixed solution of palladium nitrate and copper nitrate. The amount of solution was calculated so that the pores of the support were filled; about 2500 ml of solution were required for 5 kg of the support. When all the solution had been taken up, the catalyst was dried at 120° C. and calcined at 500° C. Its composition was:

0.5% by weight of Pd
0.25% by weight of CuO
Remainder $Al_2O_3$

Catalyst B (Comparative Example)

The procedure was as in the preparation of catalyst A, but a mixed solution of palladium nitrate and zinc nitrate was used for the impregnation. The catalyst composition was:

0.5% by weight of Pd 0.25% by weight of ZnO

Remainder Al$_2$O$_3$.

Catalyst C (Comparative Example)

The procedure was as in the preparation of catalyst A, but a mixed solution of palladium nitrate, cadmium nitrate and zinc nitrate was used for the impregnation. The catalyst composition was:

0.5% by weight of Pd 0.11% by weight of CdO 0.12% by weight of ZnO

Remainder Al$_2$O$_3$.

Catalyst D

The procedure was as in the preparation of catalyst A, but a mixed solution of palladium nitrate, copper nitrate and zinc nitrate was used for the impregnation. The catalyst composition was:

0.5% by weight of Pd 0.12% by weight of CuO 0.12% by weight of ZnO

Remainder Al$_2$O$_3$.

Catalyst E

The procedure was as in the preparation of catalyst A, but a mixed solution of palladium nitrate, silver nitrate and zinc nitrate was used for the impregnation. The catalyst composition was:

0.5% by weight of Pd 0.11% by weight of Ag$_2$O 0.12% by weight of ZnO

Remainder Al$_2$O$_3$.

Catalyst F

The procedure was as in the preparation of catalyst D, but pulverulent, precipitated calcium carbonate was impregnated. The amount of solution required was about 2500 ml for 5 kg of support. The catalyst composition was:

0.5% by weight of Pd 0.11% by weight of CuO 0.11% by weight of ZnO

Remainder CaCO$_3$

Catalyst G

The procedure was as in the preparation of catalyst D, but precipitated magnesium oxide which had been converted to a particle size of 100–300 μm by compaction and screening was impregnated. The catalyst composition was:

0.5% by weight of Pd 0.10% by weight of CuO 0.10% by weight of ZnO

Remainder MgO.

TABLE 1

Catalyst testing (small autoclave)

| Catalyst | Active components | Support | Hydrogenation time min. |
|---|---|---|---|
| A Comparison | Pd/Cu | Al$_2$O$_3$ | 87 |
| B Comparison | Pd/Zn | Al$_2$O$_3$ | 62 |
| C Comparison | Pd/Zn/Cd | Al$_2$O$_3$ | 86 |
| D Invention | Pd/Zn/Cu | Al$_2$O$_3$ | 48 |
| E Invention | Pd/Zn/Ag | Al$_2$O$_3$ | 69 |
| F Invention | Pd/Zn/Cu | CaCO$_3$ | 59 |
| G Invention | Pd/Zn/Cu | MgO | 114 |

Byproducts in the hydrogenation product

| Catalyst | Butanediol | "Acetal" area % | Butynediol area % | Total area % |
|---|---|---|---|---|
| A Comparison | 1.30 | 0.3 | 1.60 | 3.2 |
| B Comparison | 3.1 | 0.7 | 0.1 | 3.9 |
| C Invention | 1.6 | 0.35 | 1.3 | 3.25 |
| D Invention | 1.3 | 0.3 | 0.8 | 2.4 |
| E Invention | 2.0 | 0.5 | 0.1 | 2.6 |
| F Invention | 0.9 | 0.14 | 0.1 | 1.14 |
| G Invention | 2.1 | 0.2 | 0 | 2.3 |

Catalyst Testing

The hydrogenation experiments were carried out at 100° C. and 18 bar in a small autoclave fitted with a magnetic lifting stirrer. The starting material used was 125 ml of crude butynediol solution to which 150 mg of catalyst had been added. The hydrogen consumption was monitored through the drop in pressure in the autoclave; the hydrogen it consumed was replaced periodically. Due to the difficulty in recognizing the end point in the selective hydrogenation to butenediol, somewhat higher byproduct values were generally found than in the production plant, which allows better recognition of the end point.

The hydrogenation product was analyzed by gas chromatography; the results are given in area percent. The first cut amounts were independent of the catalyst and given by the quality of the crude butynediol.

The data for the hydrogenation product are shown in Table I. The residue amounts were only measured for catalysts B, C and D and were, in each case based on 100 g of hydrogenation product:

17.5 g for catalyst B 10.8 g for catalyst C 12.9 g for catalyst D.

The results are means from five experiments.

Hydrogenation Results From a Production Plant

Catalysts B, C and D were subjected to long-term testing on an industrial scale. Butynediol hydrogenation was carried out batchwise by the suspension method. 1 kg of catalyst was employed per m$^3$ of crude butynediol.

The byproduct content, given in area percent of the gas chromatographic analysis, was determined as follows:

| Catalyst | Butanediol | "Acetal" | Butynediol | Total (an + ac + in) |
|---|---|---|---|---|
| B | 1.34% | 0.47% | 0.35% | 2.16% |
| C | 0.94% | 0.37% | 0.53% | 1.84% |
| D | 0.83% | 0.33% | 0.29% | 1.45% |

These data confirm the advantages given by using the novel catalyst D.

We claim:

1. A process for the preparation of 2-butene-1,4-diol by hydrogenation of butynediol in the presence of a palladium catalyst, wherein a catalyst is used which, in addition to palladium, contains the elements zinc and copper or zinc and silver or zinc and copper and silver.

2. A process as claimed in claim 1, wherein a palladium supported catalyst having a palladium content of from 0.1 to 7% by weight, calculated as Pd and based on the total weight of the catalyst, is used.

3. A process as claimed in claim 1, wherein a palladium supported catalyst is used in which the atomic ratio between the catalytically active element is palladium:zinc 10:1 to 1:4 and zinc: copper 5:1 to 1:2.

4. A process as claimed in claim 1, wherein a palladium supported catalyst is used in which the atomic ratio between the catalytically active elements is palladium:zinc 10:1 to 1:4 and zinc:silver 5:1 to 1:2.

5. A process as claimed in claim 1, wherein a palladium supported catalyst is used in which the atomic ratio between the catalytically active elements is palladium:zinc 10:1 to 1:4 zinc:copper 5:1 to 1:2 and zinc: silver 5:1 to 1:2.

6. A process as claimed in claim 1, wherein a palladium supported catalyst is used in which the catalytically active elements have been applied to a basic or low-acidity support material.

7. A process as claimed in claim 1, wherein a palladium supported catalyst on a support of aluminum oxide, calcium carbonate, magnesium oxide, spinel, barium sulfate, titanium dioxide, zirconium dioxide or mixtures thereof is used.

8. A process as claimed in claim 1, wherein a palladium supported catalyst on a support of δ-aluminum oxide is used.

9. A process as claimed in claim 1, wherein the reaction is carried out at from 20° to 150° C. and from 1 to 20 bar.

10. A process as claimed in claim 1, wherein the starting material is a solution of crude butynediol from the Reppe synthesis.

* * * * *